United States Patent [19]

Näf et al.

[11] 4,447,627

[45] May 8, 1984

[54] ALIPHATIC EPOXY-KETONE

[75] Inventors: Regula Näf, Carouge; Anthony F. Morris, Gingins; Ferdinand Näf, Carouge, all of Switzerland

[73] Assignee: Firmenich SA, Geneva, Switzerland

[21] Appl. No.: 370,870

[22] Filed: Apr. 22, 1982

[30] Foreign Application Priority Data

Jun. 11, 1981 [CH] Switzerland ......................... 3822/81

[51] Int. Cl.³ ........................................... C07D 303/32
[52] U.S. Cl. .................................. 549/548; 252/522 R
[58] Field of Search ......................................... 549/548

[56] References Cited

PUBLICATIONS

R. Naef-Mueller et al., Helv. Chim. Acta (1981), vol. 64(5), pp. 1424–1430.

*Primary Examiner*—Norma S. Milestone
*Attorney, Agent, or Firm*—Pennie & Edmonds

[57] ABSTRACT 5,6-Epoxy-3,3,6-trimethyl-hept-1-en-4-one, a novel aliphatic epoxy-ketone, has been found to possess useful odor and flavor properties. It can be advantageously used as perfume and flavor-modifying ingredient.

Perfume and flavor-modifying composition containing same and process for its preparation.

1 Claim, No Drawings

ALIPHATIC EPOXY-KETONE

SUMMARY OF THE INVENTION

One of the objects of the invention is to provide a new composition of matter, namely 5,6-epoxy-3,3,6-trimethyl-hept-1-en-4-one.

A further object of the invention is a method for improving, enhancing or modifying the odor properties of perfumes, perfume bases or perfumed products, or the flavor properties of foodstuffs, beverages, pharmaceutical preparations or tobacco products, which comprises the step of adding thereto an organoleptically effective amount of 5,6-epoxy-3,3,6-trimethyl-hept-1-en-4-one.

The invention also relates to a perfume or flavor-modifying composition containing said 5,6-epoxy-3,3,6-trimethyl-hept-1-en-4-one as organoleptically active ingredient.

The invention finally relates to a process for preparing 5,6-epoxy-3,3,6-trimethyl-hept-1-en-4-one which comprises (a) adding 3-methyl-but-2-enyl chloride to 3-methyl-but-2-en-1-oyl chloride in the conditions of a Grignard reaction and subsequently hydrolyzing the obtained reaction mixture, and (b) epoxidizing, in basic medium, the 3,3,6-trimethyl-hepta-1,5-dien-4-one thus prepared.

BACKGROUND OF THE INVENTION

It has been surprisingly found that 5,6-epoxy-3,3,6-trimethyl-hept-1-en-4-one, a new chemical entity having the formula

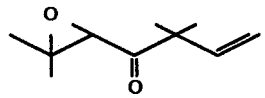

possessed very interesting organoleptic properties and that it could have a utility as fragrant and flavor-modifying ingredient.

It has been found, in particular, that it could be advantageously used for developing or enhancing herbal, aromatic and camphor-like odor notes reminiscent of certain nuances typical of the odor of artemisia (Artemisia vulgaris), rosemary, tobacco, tea, hay or even sage.

It has also been found that 5,6-epoxy-3,3,6-trimethyl-hept-1-en-4-one, could be used for developing green and flowery aroma notes, reminiscent of that of fennel.

PREFERRED EMBODIMENTS OF THE INVENTION

In view of its original odor properties, 5,6-epoxy-3,3,6-trimethyl-hept-1-en-4-one is particularly useful for the preparation of perfumes, perfume bases or perfumed products such as soaps, powder or liquid detergents, cosmetic preparations or household material such as waxes for example.

In order to achieve particular odor effects such as those described above, 5,6-epoxy-3,3,6-trimethyl-hept-1-en-4-one can be used either in its pure state or in combination with one or several perfuming coingredients, a convenient diluent or carrier. Interesting odor effects may be achieved by making use of proportions comprised between about 0.2 and 20% by weight of a given perfume base for example. Smaller proportions can also be used, namely for perfuming soaps, detergents or household materials for example.

Such concentrations, however, must not be interpreted in a restricted way, as they may obviously depend on the nature of the coingredients of a given perfume of flavor-modifying composition or the nature of the article to be perfumed or flavored.

According to one of the embodiments of the invention 5,6-epoxy-3,3,6-trimethyl-hept-1-en-4-one can be prepared by (a) adding 3-methyl-but-2-enyl chloride to 3-methyl-but-2-en-1-oyl chloride in the conditions of a Grignard reaction and subsequently hydrolyzing the obtained reaction mixture, and (b) epoxidizing, in basic medium, the 3,3,6-trimethyl-hepta-1,5-dien-4-one thus prepared.

Such a preparative process can be visualized as follows:

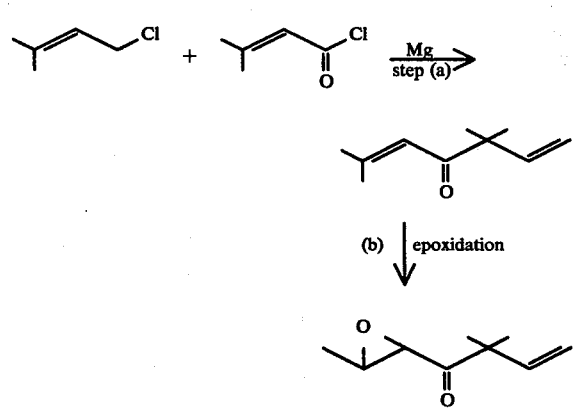

Both reaction steps (a) and (b) can be effected in accordance with the techniques usual in the art. The so-called Grignard addition (step a) is more conveniently effected in an ether solvent, preferably tetrahydrofurane. The subsequent epoxidation reaction (step b) can be carried out with the usual epoxidizing agents: the best yields of final product have been achieved by making use of a methanolic solution of hydrogen peroxide, in basic medium.

The invention will be illustrated, but not limited thereto, by the following examples wherein the temperature are given in degrees centigrade and the abbreviations used have the definition usual in the art.

EXAMPLE 1

Preparation of 5,6-epoxy-3,3,6-trimethyl-hept-1-en-4-one (a) 3 g of 3-methyl-but-2-enyl chloride (prenyl chloride) were added, under stirring, to a suspension of magnesium turnings (20 g; 0.83 M) in 100 ml of absolute tetrahydrofurane (THF). After initiation of the reaction, there were still added 900 ml of THF and the whole mixture was then cooled to $-5°$. A solution of 80 g of prenyl chloride in 400 ml of THF was then added to the above mixture which was finally kept at 10° for 3 hours. After cooling to 0°, a solution of 83 g. (0.7 M) of 3-methyl-but-2-en-1-oyl chloride in 350 ml of THF was added thereto and, after having been kept at room temperature for 3 further hours, the reaction mixture was poured onto ice-water. After evaporation of the volatile parts (THF) under reduced pressure, the concentrated residue was extracted twice with diethyl ether and the combined organic extracts washed with water, then neutralized with sodium hydrogencarbonate, dried and concentrated. The crude material thus obtained was finally distilled through a VIGREUX column to yield 55.0 g of 3,3,6-trimethyl-hepta-1,5-dien-4-one having b.p. 70°–75°/11 Torr.

(b) A mixture of 20 g (0.13 M) of the above prepared ketone in 130 ml of methanol and 45 g (0.4 M) of a 30% aqueous solution of $H_2O_2$ was cooled to $-10°$. 10.8 ml of 6 N aqueous sodium hydroxyde was then added, under vigourous stirring, to the cold mixture over a period of 1½ hours: the reaction temperature progressively raised 0° and was kept at this value for 20 further hours. The reaction mixture was then poured onto ice-water and acidified with 10% aqueous sulfuric acid. After evaporation of the volatile parts under reduced pressure, the obtained residue was diluted with diethyl ether and the obtained solution then dried, concentrated and finally distilled through a VIGREUX column to afford the desired epoxyde having b.p. 92°–95°/12 Torr (purity: ca. 90%). An analytical sample was purified by a further distillation on a FISHER type column: it was characterized as follows NMR (360 MHz): 1.0 (3H, s); 1.18 (3H, s); 1.20 (3H, s); 1.42 (3H, s); 3.7 (1H, s); 5.27–5.95 (3H, m) δ ppm;

MS: $M^+=168(0.5)$; m/e: 41(100), 69(87), 43(54), 83(16), 96(16), 27(14), 111(6), 153(6), 126(5).

EXAMPLE 2

Perfume composition

A base perfume composition of "fougère" type was prepared by mixing the following ingredients (parts by weight):

| | |
|---|---|
| Linalyl acetate | 185 |
| Linalol | 278 |
| Geraniol | 130 |
| Amyl salicylate | 185 |
| Coumarin | 92.5 |
| EXALTEX ®[1] | 92.5 |
| Methyl-β-orcinate 10%* | 37 |
| Total | 1000 |

*in diethyl phthalate
[1]Pentadecanolide (origin: FIRMENICH SA, Geneva-Switzerland)

By adding 2.8 g of the compound prepared according to Example 1 to 100 g of the above base, there was obtained a new perfume composition the odor character of which was more natural and which presented a richer hay-like tonality.

What we claim is:
1. Substantially pure 5,6-Epoxy-3,3,6-trimethyl-hept-1-en-4-one.

* * * * *